(12) United States Patent
Patton

(10) Patent No.: US 8,197,420 B2
(45) Date of Patent: Jun. 12, 2012

(54) SYSTEMS AND METHODS FOR PARENTERALLY PROCURING BODILY-FLUID SAMPLES WITH REDUCED CONTAMINATION

(75) Inventor: Richard G. Patton, Seattle, WA (US)

(73) Assignee: Magnolia Medical Technologies, Inc., Seattle, WA (US)

(*) Notice: Subject to any disclaimer, the term of this patent is extended or adjusted under 35 U.S.C. 154(b) by 798 days.

(21) Appl. No.: 11/955,635

(22) Filed: Dec. 13, 2007

(65) Prior Publication Data
US 2008/0145933 A1 Jun. 19, 2008

Related U.S. Application Data

(60) Provisional application No. 60/870,599, filed on Dec. 18, 2006.

(51) Int. Cl.
*A61B 5/00* (2006.01)
*B65D 81/00* (2006.01)
(52) U.S. Cl. ........................ 600/579; 600/573
(58) Field of Classification Search .......... 600/562–584; 604/4.01, 6.15, 6.16, 403–416
See application file for complete search history.

(56) References Cited

U.S. PATENT DOCUMENTS

| | | |
|---|---|---|
| 2,707,953 A | 5/1955 | Ryan |
| 3,013,557 A | 12/1961 | Pallotta |
| 3,098,016 A | 7/1963 | Cooper et al. |
| 3,382,865 A | 5/1968 | Worral, Jr. |
| 3,405,706 A | 10/1968 | Cinqualbre |
| 3,494,351 A | 2/1970 | Horn |
| 3,577,980 A | 5/1971 | Cohen |
| 3,648,684 A | 3/1972 | Barnwell et al. |
| 3,848,579 A | 11/1974 | Villa-Real |
| 3,937,211 A | 2/1976 | Merten |
| 4,057,050 A | 11/1977 | Sarstedt |
| 4,133,863 A | 1/1979 | Koenig |
| 4,166,450 A | 9/1979 | Abramson |
| 4,340,067 A | 7/1982 | Rattenborg |
| 4,370,987 A | 2/1983 | Bazell et al. |
| 4,444,203 A | 4/1984 | Engelman |
| 4,459,997 A | 7/1984 | Sarstedt |
| 4,509,534 A | 4/1985 | Tassin, Jr. |
| 4,676,256 A | 6/1987 | Golden |
| 4,865,583 A | 9/1989 | Tu |
| 4,890,627 A | 1/1990 | Haber et al. |
| 4,988,339 A | 1/1991 | Vadher |
| 5,009,847 A | 4/1991 | Solomons |

(Continued)

OTHER PUBLICATIONS

Wagner, S.J. et al. "Diversion of initial blood flow to prevent whole-blood contamination by skin surface bacteria: an in vitro model," Transfusion, vol. 40, Mar. 2000, pp. 335-338.

(Continued)

*Primary Examiner* — Jeffrey G Hoekstra
(74) *Attorney, Agent, or Firm* — Cooley LLP

(57) ABSTRACT

The present invention is directed to the parenteral procurement of bodily-fluid samples. The present invention is also directed to systems and methods for parenterally procuring bodily-fluid samples with reduced contamination from dermally-residing microbes. In some embodiments, a bodily-fluid withdrawing system is used to withdraw bodily fluid from a patient for incubation in culture media in one or more sample vessels. Prior to withdrawing bodily fluid into the one or more sample vessels for incubation, an initial volume of withdrawn bodily fluid is placed in one or more pre-sample reservoirs and is not used for the incubation in culture media.

17 Claims, 9 Drawing Sheets

U.S. PATENT DOCUMENTS

| | | |
|---|---|---|
| 5,097,842 A | 3/1992 | Bonn |
| 5,108,927 A | 4/1992 | Dorn |
| 5,122,129 A | 6/1992 | Olson et al. |
| 5,269,317 A | 12/1993 | Bennett |
| 5,360,011 A | 11/1994 | McCallister |
| 5,429,610 A | 7/1995 | Vaillancourt |
| 5,450,856 A | 9/1995 | Norris |
| 5,507,299 A | 4/1996 | Roland |
| 5,577,513 A | 11/1996 | Van Vlasselaer |
| 5,762,633 A | 6/1998 | Whisson |
| 5,882,318 A | 3/1999 | Boyde |
| 5,922,551 A | 7/1999 | Durbin et al. |
| 6,016,712 A | 1/2000 | Warden et al. |
| 6,057,105 A | 5/2000 | Hoon et al. |
| 6,159,164 A | 12/2000 | Neese et al. |
| 6,210,909 B1 | 4/2001 | Guirguis |
| 6,364,890 B1 | 4/2002 | Lum et al. |
| 6,387,086 B2 * | 5/2002 | Mathias et al. ............... 604/409 |
| 6,403,381 B1 | 6/2002 | Mann et al. |
| 6,692,479 B2 | 2/2004 | Kraus et al. |
| 6,746,420 B1 | 6/2004 | Prestidge et al. |
| 6,913,580 B2 | 7/2005 | Stone |
| 7,044,941 B2 | 5/2006 | Mathias et al. |
| 7,087,047 B2 | 8/2006 | Kraus et al. |
| 2002/0002349 A1 | 1/2002 | Flaherty et al. |
| 2002/0183651 A1 | 12/2002 | Hyun |
| 2003/0055381 A1 | 3/2003 | Wilkinson |
| 2004/0010228 A1 | 1/2004 | Swenson et al. |
| 2004/0054333 A1 | 3/2004 | Theeuwes et al. |
| 2004/0147855 A1 | 7/2004 | Marsden |
| 2005/0004524 A1 | 1/2005 | Newby et al. |
| 2005/0240161 A1 | 10/2005 | Crawford |
| 2005/0245885 A1 | 11/2005 | Brown |
| 2005/0281713 A1 | 12/2005 | Hampsch et al. |
| 2006/0287639 A1 | 12/2006 | Sharp |

OTHER PUBLICATIONS

International Search Report and Written Opinion mailed May 16, 2008, which issued during the prosecution of International Patent Application No. PCT/US2007/087951 (8 pages).

* cited by examiner

US 8,197,420 B2

SYSTEMS AND METHODS FOR PARENTERALLY PROCURING BODILY-FLUID SAMPLES WITH REDUCED CONTAMINATION

RELATED APPLICATIONS

This application claims priority to U.S. Provisional Application Ser. No. 60/870,599, filed Dec. 18, 2006, the entire contents of which is incorporated herein by reference.

TECHNICAL FIELD

The present invention is directed to the parenteral procurement of bodily-fluid samples. The present invention is also directed to systems and methods for parenterally procuring bodily-fluid samples with reduced contamination from dermally-residing microbes.

BACKGROUND

Health care professionals routinely perform various types of microbial tests on patients using parenterally-obtained patient bodily fluids. Contamination of parenterally-obtained bodily fluids by microbes may result in spurious microbial test results. Spurious microbial test results may be a concern when attempting to diagnose or treat a suspected illness or condition. False positive results from microbial tests can cause a patient to be unnecessarily subjected to one or more anti-microbial therapies, such as anti-bacterial or anti-fungal therapies, which may cause anguish and inconvenience to the patient, as well as produce an unnecessary burden and expense to the health care system.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the parenteral procurement of bodily-fluid samples. The present invention is also directed to systems and methods for parenterally procuring bodily-fluid samples with reduced contamination from dermally-residing microbes. In some embodiments, a bodily-fluid withdrawing system is used to withdraw bodily fluid from a patient for incubation in culture media in one or more sample vessels. Prior to withdrawing bodily fluid into the one or more sample vessels for incubation, an initial volume of withdrawn bodily fluid is placed in one or more pre-sample reservoirs and is not used for the incubation in culture media.

Health care professionals routinely procure parenterally-obtained bodily-fluid samples ("samples") from patients. Patient samples may include many different types of bodily fluids. For example, patient samples may include blood, cerebrospinal fluid, urine, bile, lymph, saliva, synovial fluid, serous fluid, pleural fluid, amniotic fluid, and the like. Patient samples are sometimes tested for the presence of one or more potentially undesirable microbes, such as bacteria, fungi, or *Candida*. Microbial testing may include incubating patient samples in one or more sterile vessels containing culture media that is conducive to microbial growth. Generally, when microbes tested for are present in the patient sample, the microbes flourish over time in the culture medium. After a pre-determined amount of time, the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to remove the undesired microbes from the patient.

Patient samples can sometimes become contaminated during procurement. Contamination of a patient sample may result in a spurious microbial test result which, in turn, may cause the patient to unnecessarily undergo one or more microbial-removal treatments. One way in which contamination of a patient sample may occur is by the transfer of dermally-residing microbes dislodged during needle insertion into a patient and subsequently transferred to a culture medium with the patient sample. The dermally-residing microbes may be dislodged either directly or via dislodged tissue fragments. The transferred microbes may thrive in the culture medium and eventually yield a positive microbial test result, thereby falsely indicating the presence of microbes in vivo.

Figure 1:
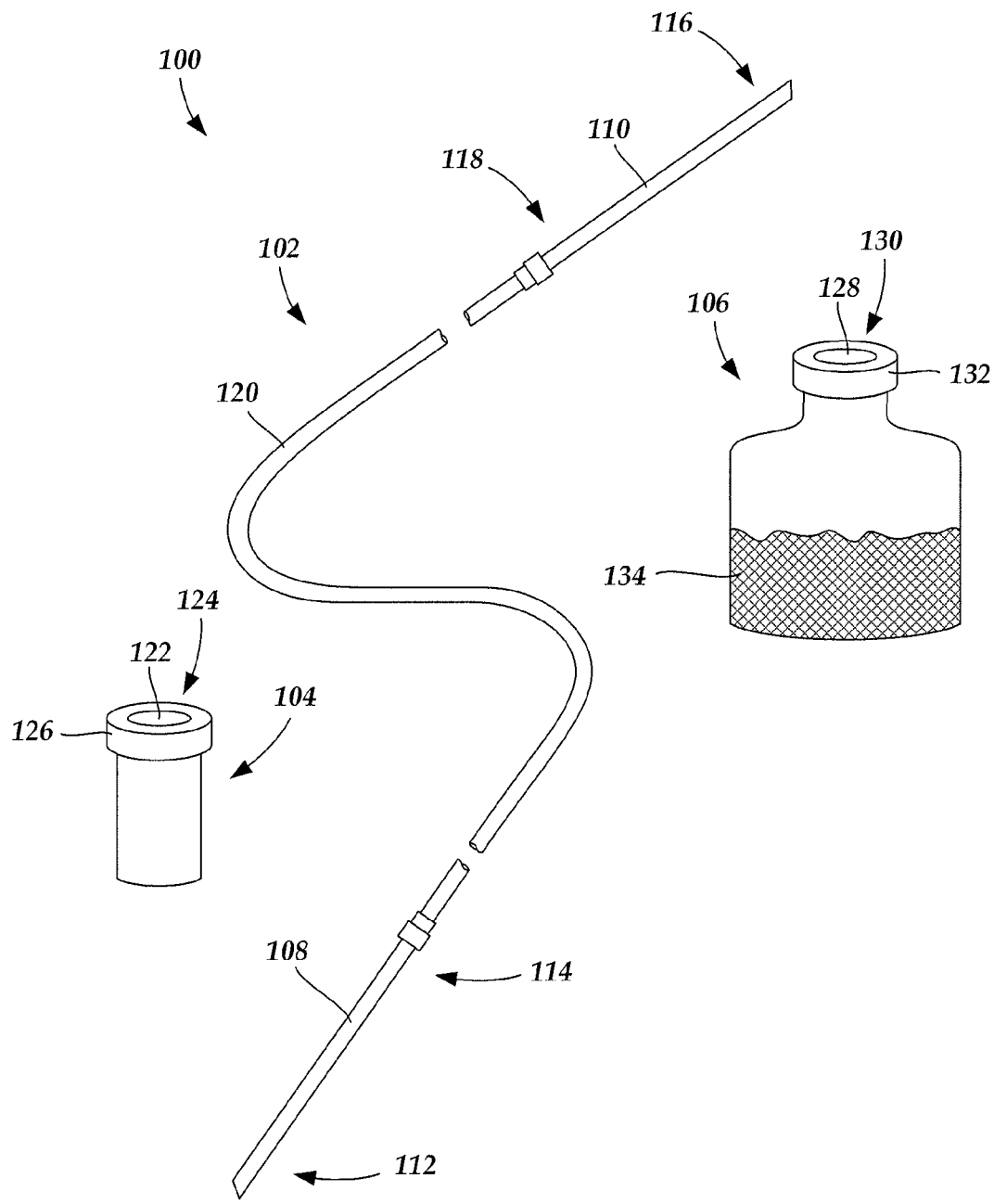
FIG. 1 is a schematic view of one embodiment of a sample-procurement system, according to the invention.

FIG. 1 is a schematic view of one embodiment of a sample-procurement system 100. The sample-procurement system 100 includes a bodily-fluid withdrawing device 102, one or more pre-sample reservoirs 104, and one or more culture-medium-containing sample vessels 106 ("sample vessels"). In FIG. 1 (and in subsequent figures), a single pre-sample reservoir 104 is shown and represents either one pre-sample reservoir 104 or a plurality of pre-sample reservoirs 104. Likewise, FIG. 1 (and subsequent figures) shows a single sample vessel 106 that represents either one sample vessel 106 or a plurality of sample vessels 106.

The bodily-fluid withdrawing device 102 includes a first sterile needle 108 ("first needle") and a second sterile needle 110 ("second needle") coupled to the first needle 108. The first needle 108 includes a distal end 112, a proximal end 114, and a lumen (see FIG. 2) extending from the distal end 112 to the proximal end 114. The distal end 112 is configured and arranged for puncturing through multiple layers of patient skin and the proximal end 114 is configured and arranged for attachment with sterile, lumen-containing devices. The lumen (see FIG. 2) is configured and arranged for passing bodily-fluids from the distal end 112 of the first needle 108 to the proximal end 114.

The second needle 110 includes a distal end 116 configured and arranged for puncturing septa disposed over pre-sample reservoirs 104 and sample vessels 106, a proximal end 118 configured and arranged for attachment with other sterile, lumen-containing devices, and a lumen (not shown) extending from the distal end 116 to the proximal end 118. The first needle 108 and the second needle 110 can be manufactured using any rigid, sterilizable, biocompatible material suitable for penetrating the skin of a patient, septa 122 disposed over pre-sample reservoir 104, or septa 128 disposed over sample vessels 106. Exemplary materials may include stainless steel, and the like. In at least some embodiments, the first needle 108 and the second needle 110 are selected from the Vacu-tainer™ blood collection set, manufactured by Becton Dickinson.

In at least some embodiments, the proximal end 114 of the first needle 108 couples directly to the proximal end 118 of the second needle 110. In other embodiments, the proximal end 114 of the first needle 108 couples, via one or more sterile, intermediary, lumen-containing devices, to the proximal end 118 of the second needle 110. In FIG. 1, a flexible sterile tubing 120 is shown coupling the proximal end 114 of the first needle 108 to the proximal end 118 of the second needle 110. The sterile tubing 120 can be manufactured using any flexible, sterilizable, biocompatible material suitable for containing bodily fluids. Exemplary materials may include plastic, silicone rubber, and the like.

Each of the one or more pre-sample reservoirs 104 is sterile and includes a septum 122 covering a mouth 124 of each of the pre-sample reservoirs 104. Each septum 122 seals the mouth 124 and maintains an internal vacuum inside the pre-sample reservoir 104. In at least some embodiments, the septum 122 is held in place by a crimp ring 126. Likewise, each of the one or more sample vessels 106 is sterile and includes an internal vacuum maintained by a septum 128 covering a mouth 130 of each of the one or more sample vessels 106. In at least some embodiments, the septum 128 is held in place by a crimp ring 132. The one or more pre-sample reservoirs 104 and the one or more sample vessels 106 can be manufactured using any sterilizable, biocompatible material suitable for containing bodily fluids and culture media, or any other testing additives. Exemplary materials may include glass, plastic, and the like. In at least one embodiment, the first needle 108, the second needle 110, the sterile tubing 120, the one or more pre-sample reservoirs 104, and one or more sample vessels 106 are all disposable.

Each of the one or more sample vessels 106 contains a culture medium 134 for growing selected microbes. A culture medium may contain different amounts of different components, depending on the type of microbes being detected. A culture medium may include, for example, a nutrient broth with a carbon source, a nitrogen source, salts, water, and an amino acid source. Additionally, sample vessels undergoing microbial testing may be incubated at a specific temperature to further facilitate growth of a tested microbe.

Figure 2:
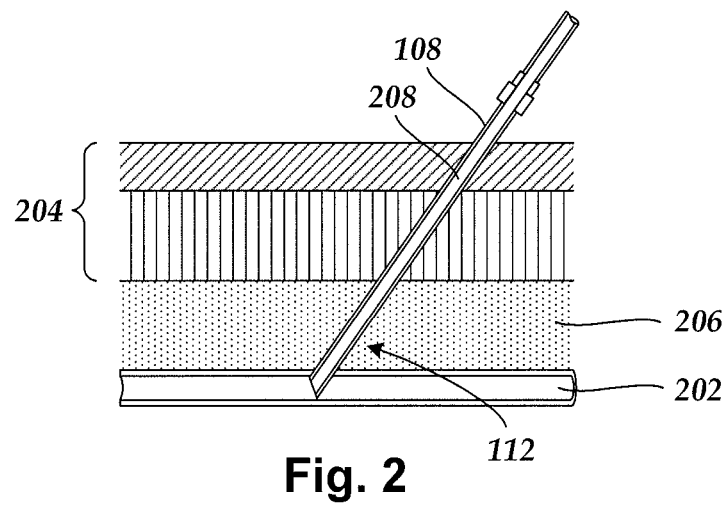
FIG. 2 is a schematic cross-sectional view of one embodiment of a first needle of a sample-procurement system inserted into a patient vein; according to the invention.

Examples of the sample-procurement system are shown in FIGS. 1-7, and also discussed in reference to FIGS. 1-7, in terms of procuring blood samples from a patient vein. Procuring blood from a patient vein is meant to serve as one of many possible types of bodily fluids parenterally withdrawn from one of many possible body locations. FIG. 2 is a schematic cross-sectional view of the first needle 108 inserted into a lumen of a vein 202 of a patient. The distal end 112 of the first needle 108 is shown extending through multiple layers of skin 204 and a layer of subcutaneous fat 206. The first needle 108 includes a lumen 208 extending along the length of the first needle 108. When the distal end 112 of the first needle 108 is inserted into a fluid-containing portion of a body, such as the lumen of the vein 202, fluid within the fluid-containing portion of the body may be withdrawn from the fluid-containing portion of the body by passing the fluid through the lumen 208 of the first needle 108.

In at least some embodiments, prior to penetration with the first needle 108 patient skin is cleansed with one or more disinfectants to reduce the number of microbes on an outer surface of the patient skin. For example, patient skin can be cleansed with a gauze pad soaked with a disinfectant. Many different types of disinfectants may be used to cleanse patient skin. In one embodiment, patient skin is cleansed with a disinfectant that includes a 70% isopropyl alcohol solution, with 2% Chlorhexidine Gluconate, manufactured by Medi-Flex, Inc.

Figure 3A:
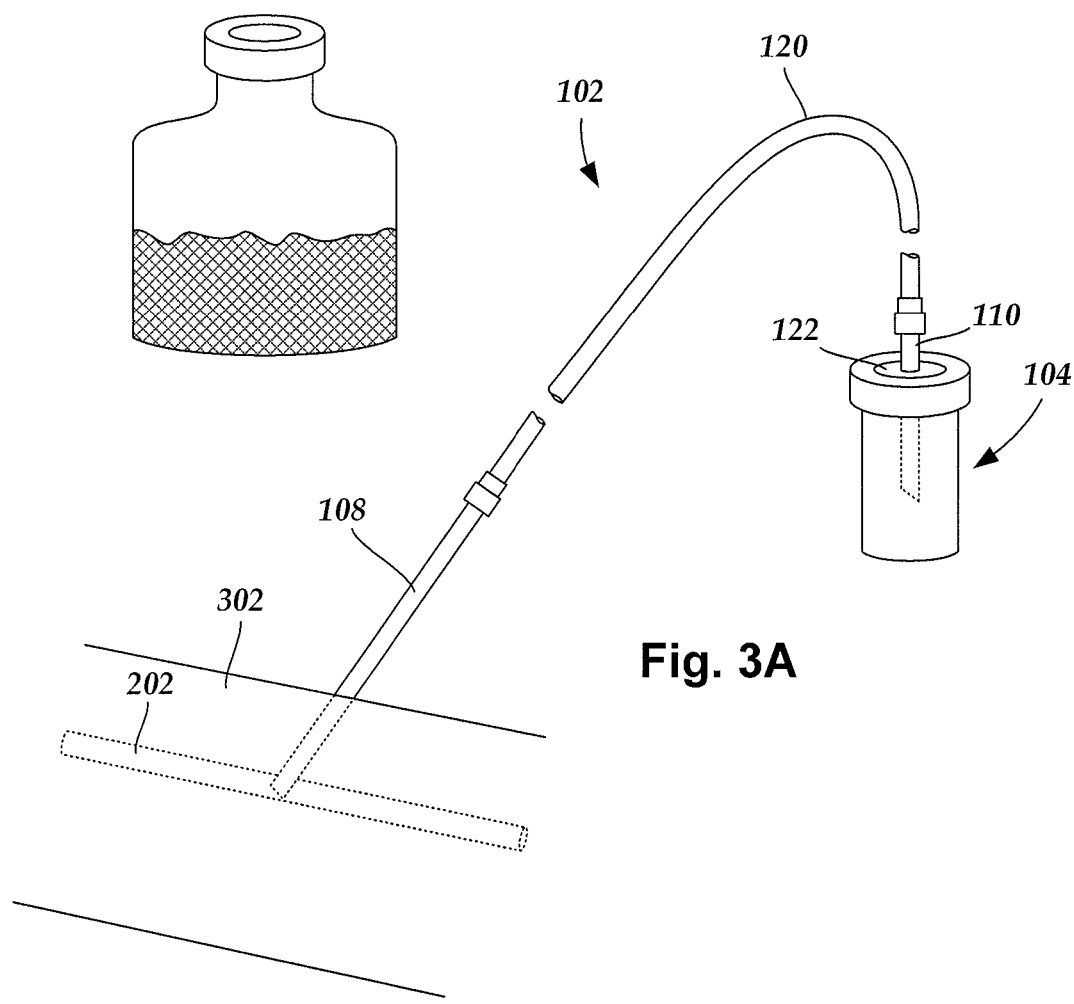
FIG. 3A is a schematic view of one embodiment of a bodily-fluid withdrawing device draining blood from a patient vein into a pre-sample reservoir, according to the invention.

Once the first needle 108 is inserted into a desired fluid-containing body location, the second needle 110 is inserted into the pre-sample reservoir 104 and blood is withdrawn into the one or more pre-sample reservoirs 104. FIG. 3A is a schematic view of one embodiment of the bodily-fluid withdrawing device 102 being used to procure blood from the vein 202 of a patient and depositing the blood in the one or more pre-sample reservoirs 104. In FIG. 3A, the first needle 108 is shown extending through a patient limb 302 and into the vein 202. The second needle 110 is in fluid communication with the first needle 108, either directly, or via one or more intermediary lumen-containing devices, such as the sterile tubing 120. The second needle 112 is inserted through the septum 122 and into the one or more pre-sample reservoirs 104, which contains an internal vacuum. In at least some embodiments, the insertion of the second needle 110 into the vacuum-sealed pre-sample reservoir 106 creates a difference in pressure between the lumen of the first needle 108 and the lumen of the second needle 110. The pressure change causes the blood from the vein 202 to be transferred into the pre-sample reservoir 104 until the pressures equalize. Once the pressures equalize between the lumen of the first needle 108 and the lumen of the second needle 110, the blood tends to stop flowing from the vein 202 to the pre-sample reservoir 104. When the blood stops flowing into the pre-sample reservoir 104, the second needle can be removed and inserted into another pre-sample reservoir or a sample reservoir.

Accordingly, the initial portion of blood withdrawn from the patient is drawn into the pre-sample reservoir 104 and is not used for cultured microbial testing. In a preferred embodiment, the amount of blood withdrawn into the pre-sample reservoir 104 is at least equal to the combined volumes of the lumen of the first needle 108, the lumen of the second needle 110, and the lumens of any intermediary lumen-containing devices, such as the sterile tubing 120. Dermally-residing microbes which may have been dislodged into the lumen of the first needle 108 during the insertion of the first needle 108 into the vein 202 may be washed into the pre-sample reservoir 104, thereby reducing the microbial contamination in the blood that is subsequently used as one or more samples for cultured microbial tests.

The amount of blood transferred to the pre-sample reservoir 104 may be regulated by the size of the pre-sample reservoir 104. For example, a relatively large pre-sample reservoir may need to draw more blood to equalize pressure than a relatively small pre-sample reservoir. In at least some embodiments, the one or more pre-sample reservoirs 104 are configured and arranged to hold approximately 1 ml to 5 ml. The pre-sample reservoirs 104 may also include one or more additives. For example, in at least some embodiments, the pre-sample reservoirs 104 are BD Vacutainers™ with buffered citrate, manufactured by Becton Dickenson.

In at least some embodiments, blood collected in one or more pre-sample reservoirs is discarded. In other embodiments, blood collected in one or more pre-sample reservoirs is used for conducting one or more non-culture tests, such as one or more biochemical tests, blood counts, immunodiagnostic tests, cancer-cell detection tests, and the like. In at least some embodiments, one or more pre-sample reservoirs may also include culture media for facilitating growth of one or more types of microbes.

Figure 3B:
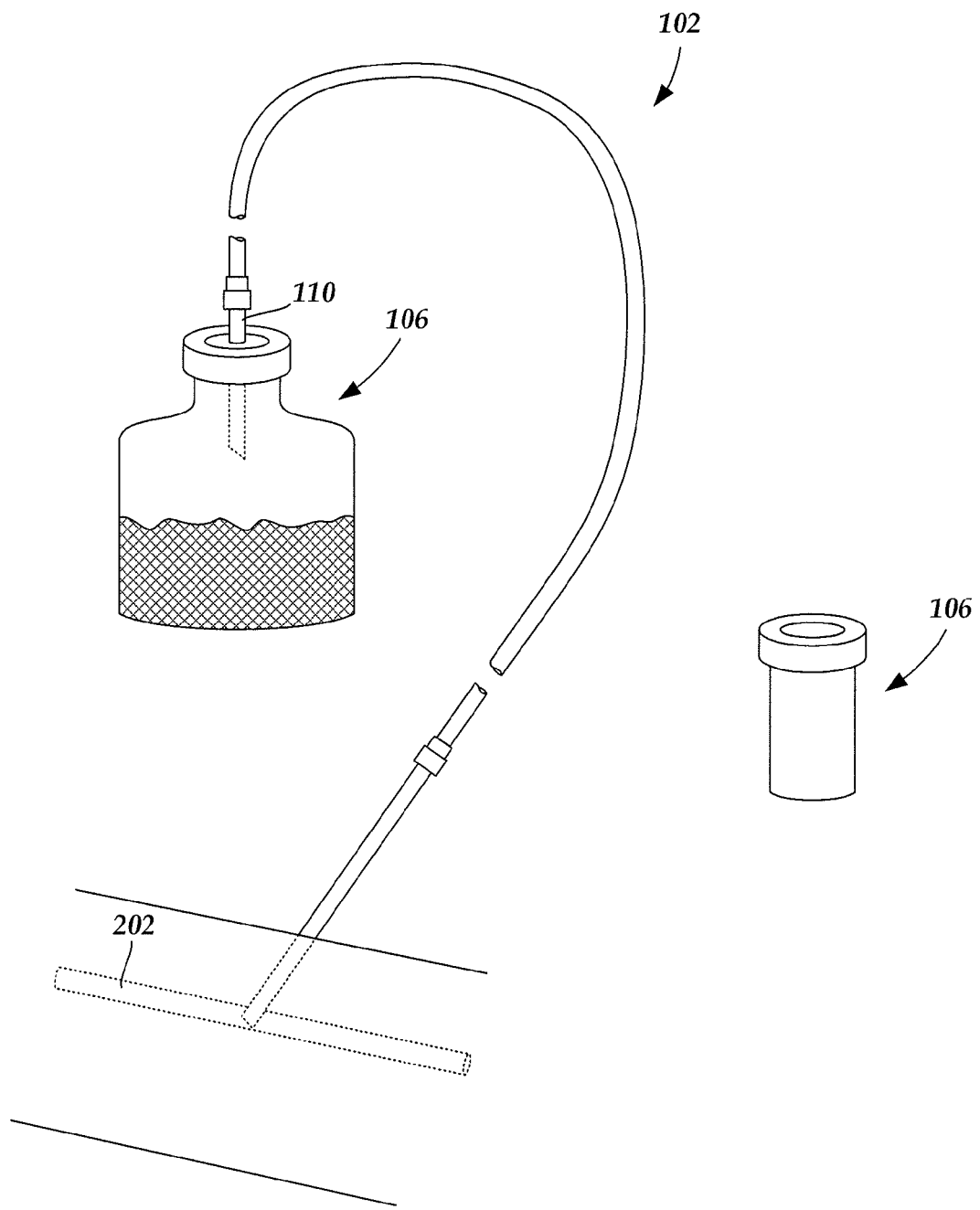
FIG. 3B is a schematic view of one embodiment of a bodily-fluid withdrawing device draining blood from a patient vein into a sample vessel, according to the invention.

Once blood has been deposited in one or more pre-sample reservoirs, the second needle 112 may be inserted into a sample vessel. FIG. 3B is a schematic view of one embodiment of the bodily-fluid withdrawing device 102 being used to procure blood from the vein 202 of a patient and depositing the blood in the sample vessel 106. In at least some embodiments, the one or more sample vessels 106 are each vacuum-sealed. In a manner similar to the one or more pre-sample reservoirs 104, the insertion of the second needle 110 into the vacuum-sealed sample vessel 106 tends to cause blood from the vein 202 to be transferred into the sample vessel 106 until the pressures equalize.

In at least some embodiments, the amount of blood collected is determined based on the size of the sample vessel or the amount of blood needed to grow the microbes, if present, in the culture medium. In at least some embodiments, the one or more sample vessels 106 are configured and arranged to receive approximately 2 ml to 10 ml of bodily fluids in a sterile solid or liquid culture medium. In at least some embodiments, the one or more sample vessels 106 include the BacT/ALERT® SN and BacT/ALERT® FA, manufactured by BIOMERIEUX, INC.

Figure 4A:
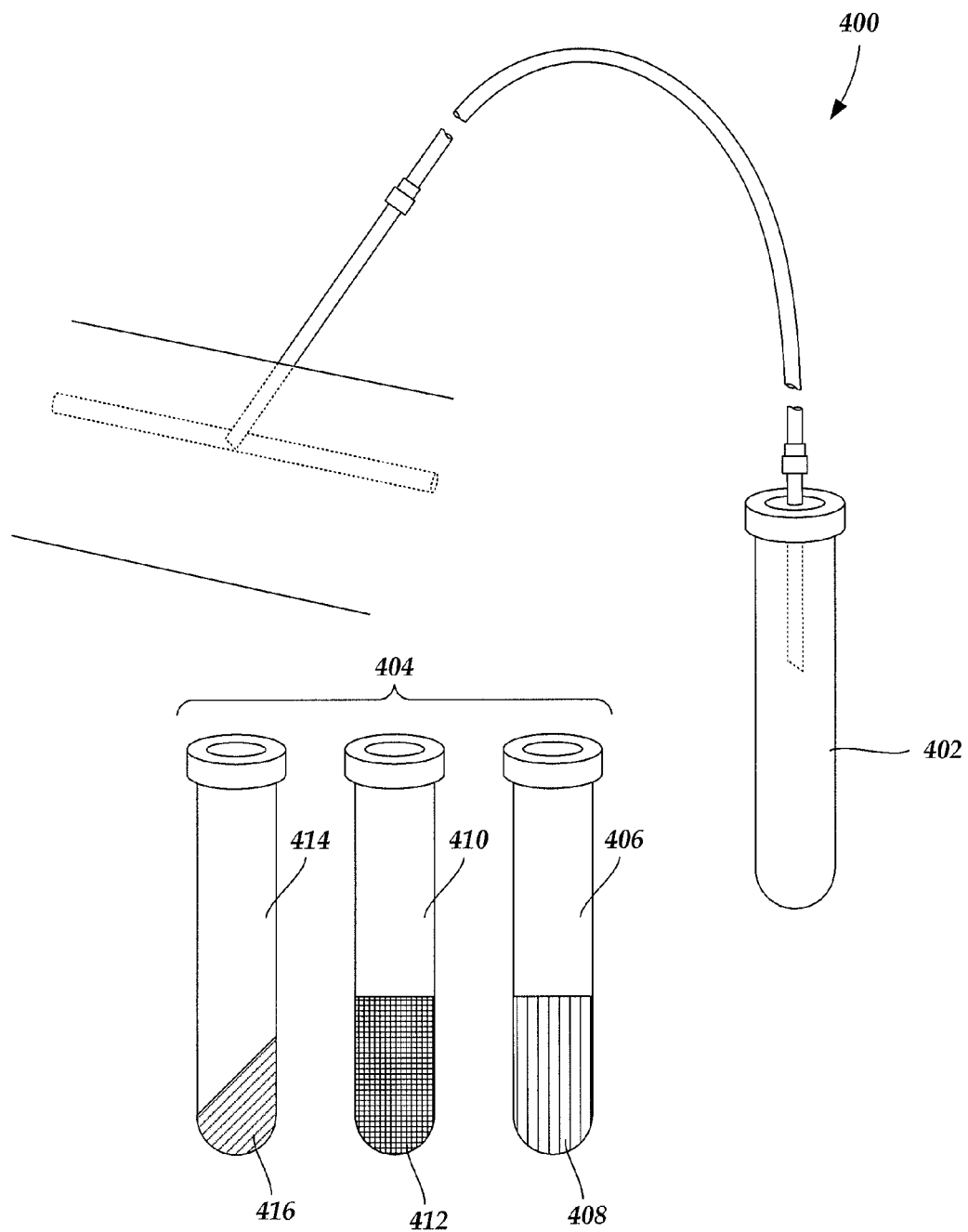
FIG. 4A is a schematic view of another embodiment of a sample-procurement system with multiple sample vessels being used to drain blood from a patient to a pre-sample reservoir, according to the invention.

As discussed above, in at least some embodiments a sample-procurement system includes one or more pre-sample reservoirs and one or more sample vessels. FIG. 4A illustrates one embodiment of a sample-procurement system 400 having a single pre-sample reservoir 402 and a plurality of sample vessels 404. The culture medium contained in each of the plurality of sample vessels 402 can be the same or can be different. For example, in FIG. 4A a first sample vessel 406 includes a sterile fluid culture broth 408 for facilitating the growth of aerobic microbes, a second sample vessel 410 includes a sterile fluid culture broth 412 for facilitating the growth of anaerobic microbes, and a third sample vessel 414 includes a sterile slant culture 416 for facilitating the growth of fungi, or other microbes.

Figure 4B:
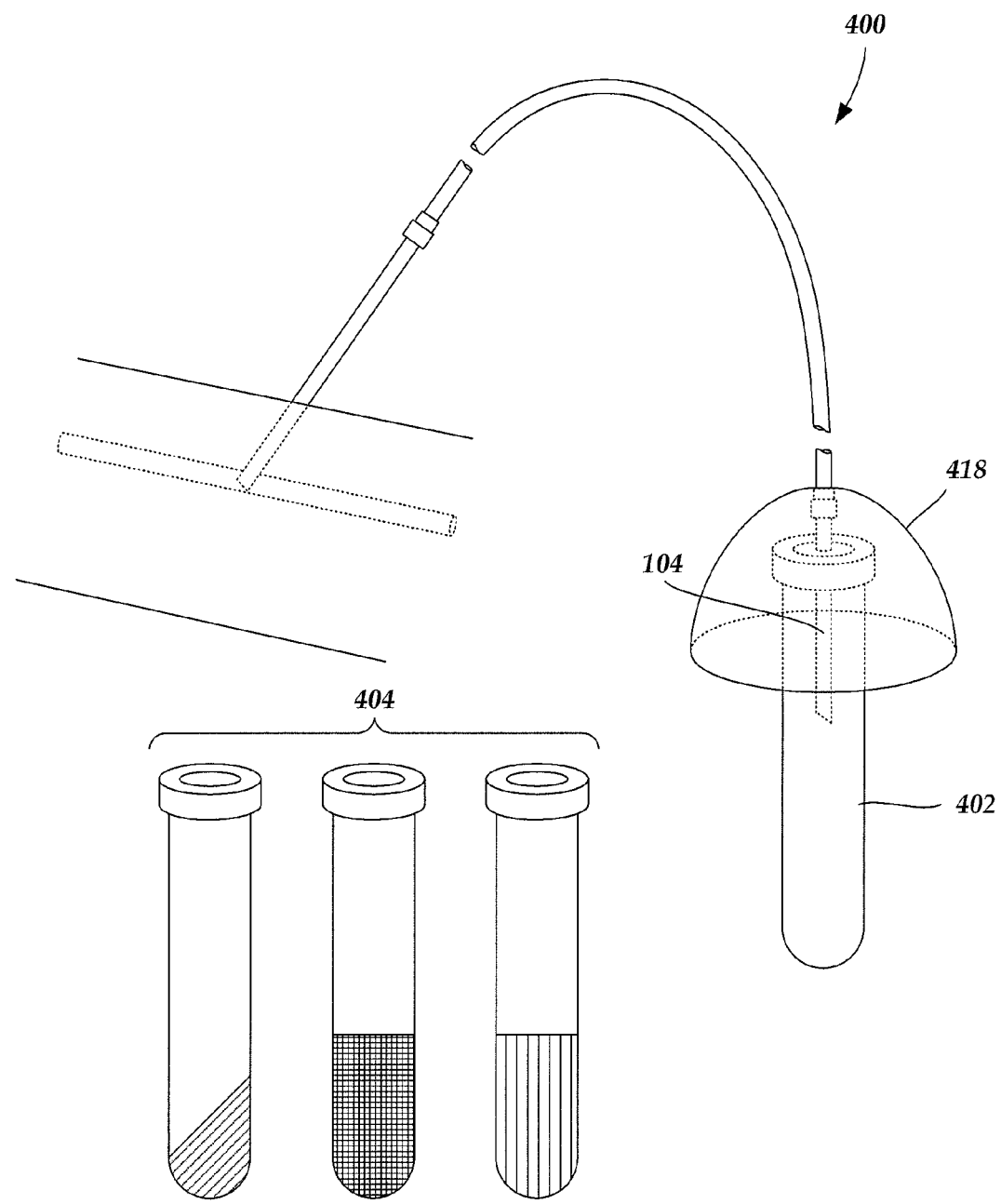
FIG. 4B is a schematic view of the embodiment of the sample-procurement system shown in FIG. 4A being used to drain blood from a patient to a pre-sample reservoir with a splash guard positioned over the second needle, according to the invention.

In at least some embodiments, a sample-procurement system can include one or more accessory devices. FIG. 4B illustrates the sample-procurement system 400 having a splash guard 418 positioned over the second needle 104. The splash guard 418 can be used to reduce the risk of undesirable blood splatter when the second needle 104 is transferred between the pre-sample reservoir 402 and each of the sample vessels 404.

Figure 5:
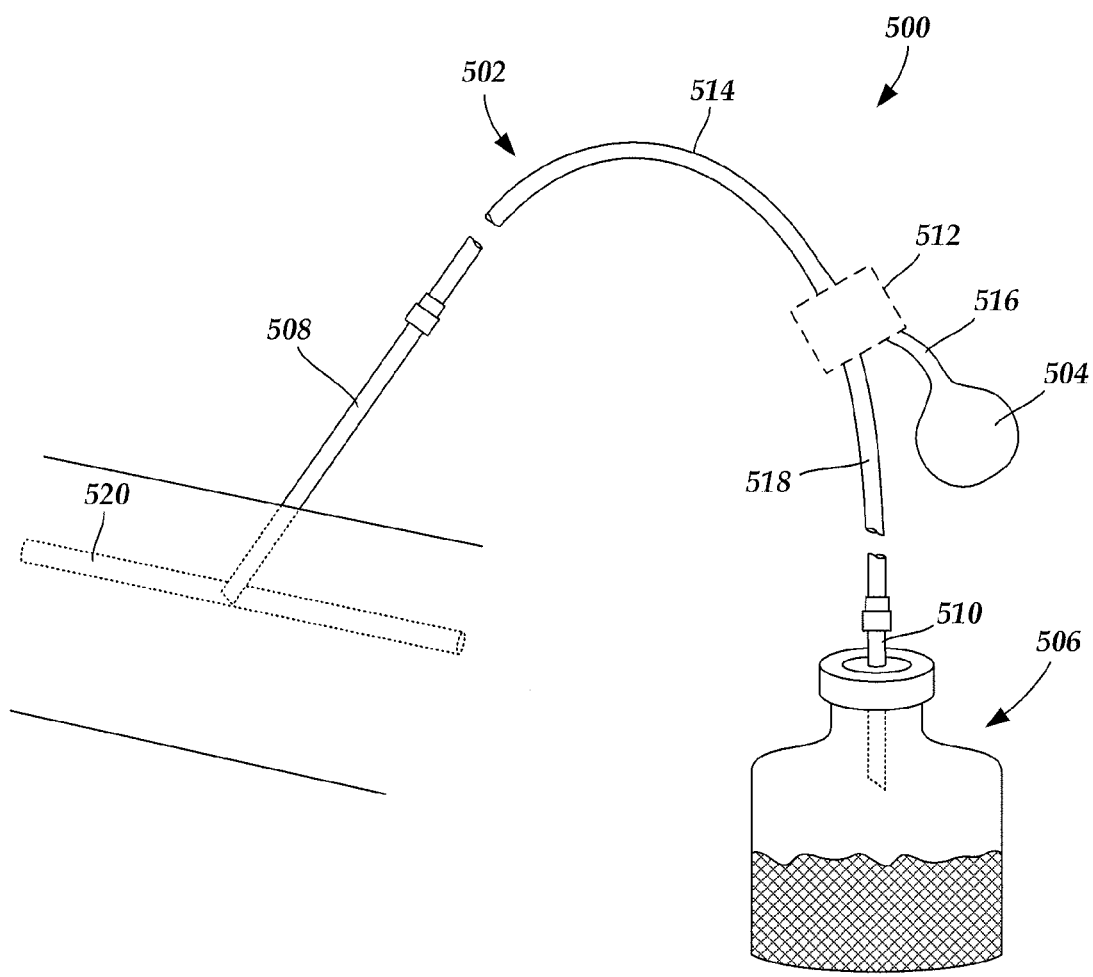
FIG. 5 is a schematic view of another embodiment of a sample-procurement system with a diversion mechanism in a bodily-fluid withdrawing device, according to the invention.

In at least some embodiments, a sample-procurement system includes a bodily-fluid withdrawing device with one or more intermediary lumen-containing devices, such as a diversion mechanism for diverting bodily fluid from the first needle to either one or more pre-sample reservoirs or to the second needle. FIG. 5 illustrates an alternate embodiment of a sample-procurement system 500. The sample-procurement system 500 includes a bodily-fluid withdrawing device 502, one or more pre-sample reservoirs 504, and one or more sample vessels 506. The bodily-fluid withdrawing device 502 includes a first needle 508, a second needle 510, a diversion mechanism 512, a flexible, sterile input tubing 514, one or more first sterile output tubing 516, and a second sterile output tubing 518.

In FIG. 5, the diversion mechanism 512 is shown as a dashed rectangle. The diversion mechanism 512 is discussed below in more detail, with reference to FIGS. 6A-7B. In at least some embodiments, the first needle 508 is coupled to the diversion mechanism 512 via the flexible, sterile input tubing 514. In at least some embodiments, the one or more pre-sample reservoirs 504 are coupled to the diversion mechanism 512 via the one or more first sterile output tubing 516. In at least some embodiments, the second needle 510 is coupled to the diversion mechanism 512 via the second sterile output tubing 518. In at least some embodiments, at least one pre-sample reservoir 504 is permanently attached to the bodily-fluid withdrawing device 502. In at least some embodiments, at least one pre-sample reservoir 504 is removably attached to the bodily-fluid withdrawing device 502. In at least some embodiments, one or more of the tubing 514, 516, and 518 are omitted and one or more of the first needle 508, the pre-sample reservoir 504, and the second needle 510, respectively, couple directly to the diversion mechanism 512.

The first needle 508 can be inserted into a patient to procure a blood sample. In FIG. 5, the first needle 508 is shown inserted into a vein 520. The second needle 510 is shown inserted into the one or more sample vessels 506 that have been vacuum-sealed. The vacuum in each of the one or more sample vessels 506 causes blood to pass from the vein 520 to the diversion mechanism 512. The diversion mechanism 512 can be adjusted to divert the flow of blood to either the one or more pre-sample reservoirs 504 or to the second needle 510 inserted into one of the one or more sample vessels 506. For example, in at least some embodiments, the diversion mechanism 512 can be initially adjusted to divert blood to the one or more pre-sample reservoirs 504 until the one or more pre-sample reservoirs 504 are filled, or a desired amount of blood has been withdrawn, at which point the diversion mechanism 512 can be adjusted to divert the flow of blood to the one or more sample vessels 506. In at least some embodiments, the volume of blood withdrawn into the one or more pre-sample reservoirs 504 is at least equal to the collective volumes of the first needle 508, the flexible, sterile input tubing 516, the diversion mechanism 512, and the first sterile output tubing 516.

Figure 6A:
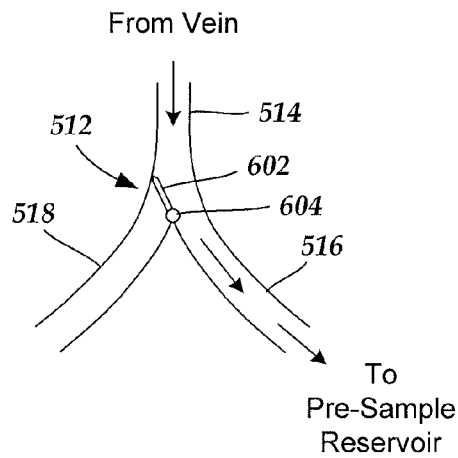
FIG. 6A is a schematic close-up view of one embodiment of a diversion mechanism that includes a switchable valve in a first position, according to the invention.

Many different types of diversion mechanisms can be used to divert the flow of bodily fluids from a patient. FIG. 6A illustrates one embodiment of the diversion mechanism 512 that includes a switchable valve 602 that pivots about a pivot point 604 positioned at the junction of the first sterile output tubing 516 and the second sterile output tubing 518. The switchable valve 602 can be placed in at least two positions: a first position (see FIG. 6A) and a second position (see FIG. 6B). When the switchable valve 602 is in a first position, as shown in FIG. 6A, the switchable valve 602 is positioned on the pivot point 604 so that the switchable valve 602 creates a seal disallowing the flow of blood input from the flexible, sterile input tubing 514 into the second sterile output tubing 518. Consequently, the blood flows into the pre-sample reservoir (not shown) via the first sterile output tubing 516.

Figure 6B:
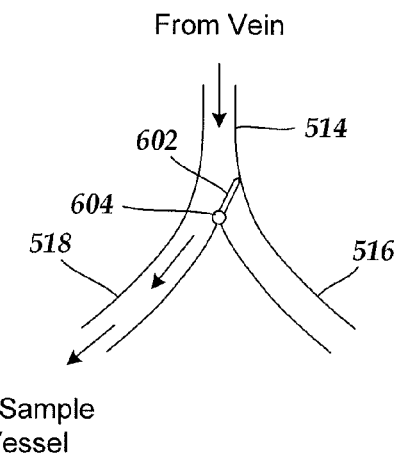
FIG. 6B is a schematic close-up view of the diversion mechanism shown in FIG. 6A in a second position, according to the invention.

FIG. 6B illustrates one embodiment of the switchable valve 602 in a second position. When the switchable valve 602 is in a second position, the switchable valve 602 is positioned on the pivot point 604 so that the switchable valve 602 creates a seal disallowing the flow of blood input from the flexible, sterile input tubing 514 into the pre-sample reservoir (not shown) via the first sterile output tubing 516. Consequently, the blood flows into the one or more sample vessels (not shown) via the second sterile output tubing 518. In at least some embodiments, the diversion mechanism 512 includes more than two positions. In which case, each position may correspond to blood-flow diversion to a unique output tubing. In some embodiments, a plurality of pre-sample reservoirs may be used. In which case, each pre-sample reservoir may correspond to a unique diversion-mechanism position. Thus, in at least some embodiments, one position corresponds to diverting blood flow to the second needle and the other positions each correspond to a unique pre-sample reservoir.

In at least some embodiments, the switchable valve can be manually switched between two or more positions by coupling an external switch to the switchable valve that can be operated either manually or electronically. In at least some embodiments, the external switch is external to each of the lumens of the bodily-fluid withdrawing device. In at least some embodiments, the switchable valve can be either manually or automatically switched between two or more of the positions by using sensors to sense when to switch a switchable valve, or timers to time when to switch a switchable valve.

Figure 7A:
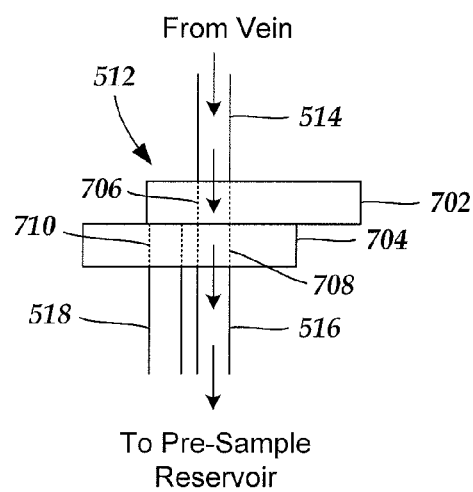
FIG. 7A is a schematic close-up view of a second embodiment of a diversion mechanism that includes two flow-control blocks in a first position, according to the invention.

FIG. 7A illustrates another embodiment of the diversion mechanism 512 that includes an input flow-control block 702 and a slidably-mounted output flow-control block 704 that slides along a shared edge with the input flow-control block 702. The input flow-control block 702 and the output flow-control block 704 can be slid back and forth between a first position (see FIG. 7A) and a second position (see FIG. 7B). The input flow-control block 702 is configured and arranged to couple with the flexible, sterile input tubing 514. The input flow-control block 702 includes a lumen 706 extending through the input flow-control block 702 from the flexible, sterile input tubing 514 to the shared edge with the output flow-control block 704.

The output flow-control block 704 is configured and arranged to couple with the first sterile output tubing 516 and the second sterile output tubing 518. The output flow-control block 704 includes a first lumen 708 extending through the output flow-control block 704 from the shared edge with the input flow-control block 702 to the first sterile output tubing 516, and a second lumen 710 also extending through the output flow-control block 704 from the shared edge with the input flow-control block 702 to the second sterile output tubing 518. When the input flow-control block 702 and the output flow-control block 704 are in a first position relative to one another, the lumen 706 on the input flow-control block 702 aligns with the first lumen 708 on the output flow-control block 704. Accordingly, the flow of blood input from the flexible, sterile input tubing 514 passes through the lumen 706 of the input flow-control block 702 and through the first lumen 708 of the output flow-control block 704 and into the pre-sample reservoir (not shown) via the first sterile output tubing 516.

Figure 7B:
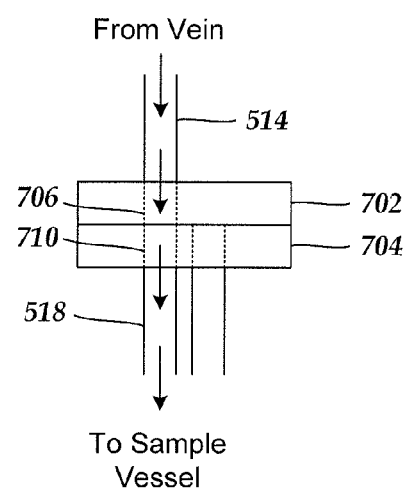
FIG. 7B is a schematic close-up view of the diversion mechanism shown in FIG. 7A in a second position, according to the invention.

In at least some embodiments, once a desired amount of blood is diverted to the one or more pre-sample reservoirs, the flow-control blocks can be slid to a second position to divert blood flow to the second needle, which may be inserted into one of the one or more sample vessels. FIG. 7B illustrates one embodiment of the input flow-control block 702 and the output flow-control block 704 in a second position. When the input flow-control block 702 and the output flow-control block 704 are in a second position relative to one another, the lumen 706 on the input flow-control block 702 aligns with the second lumen 710 on the output flow-control block 704. Accordingly, the flow of blood input from the flexible, sterile input tubing 514 passes through the lumen 706 of the input flow-control block 702 and through the second lumen 710 of the output flow-control block 704 and into the one or more sample vessels (not shown) via the second sterile output tubing 518. In at least some embodiments, the output flow-control block 704 includes additional lumens that correspond to different positions which, in turn, may correspond to blood diversion to other pre-sample reservoirs, either directly, or via one or more intermediary output tubing.

Figure 8:
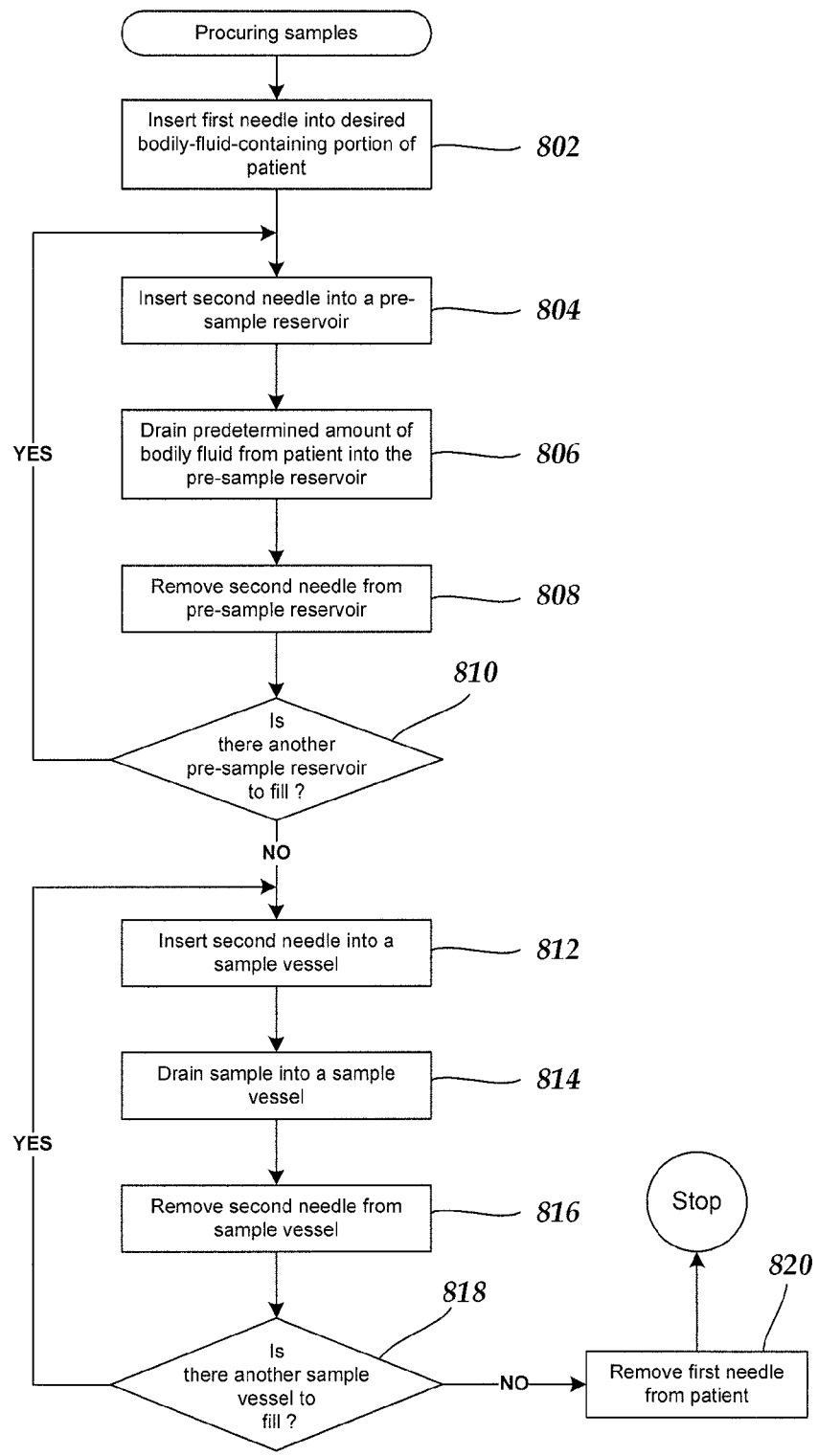
FIG. 8 illustrates a flow diagram showing one embodiment of exemplary steps used for procuring samples, according to the invention.

FIG. 8 illustrates a flow diagram showing one embodiment of exemplary steps used for procuring samples. In step 802, a first needle is inserted into a desired bodily-fluid-containing portion of a patient. In step 804, a second needle is inserted into a pre-sample reservoir. In step 806, a predetermined amount of bodily fluid is drained from the patient into the pre-sample reservoir. In step 808, the second needle is removed from the pre-sample reservoir. When, in step 810, there is another pre-sample reservoir to drain bodily fluid into, control is passed back up to step 804. Otherwise, control passes to step 812, where the second needle is inserted into a sample vessel. In step 814, a predetermined amount of bodily fluid is drained from the patient into the sample vessel. In step 816, the second needle is removed from the sample vessel. When, in step 818, there is another sample vessel to drain bodily fluid into, control is passed back up to step 812. Otherwise, in step 820 the first needle is removed from the patient and the flow ends.

Figure 9:
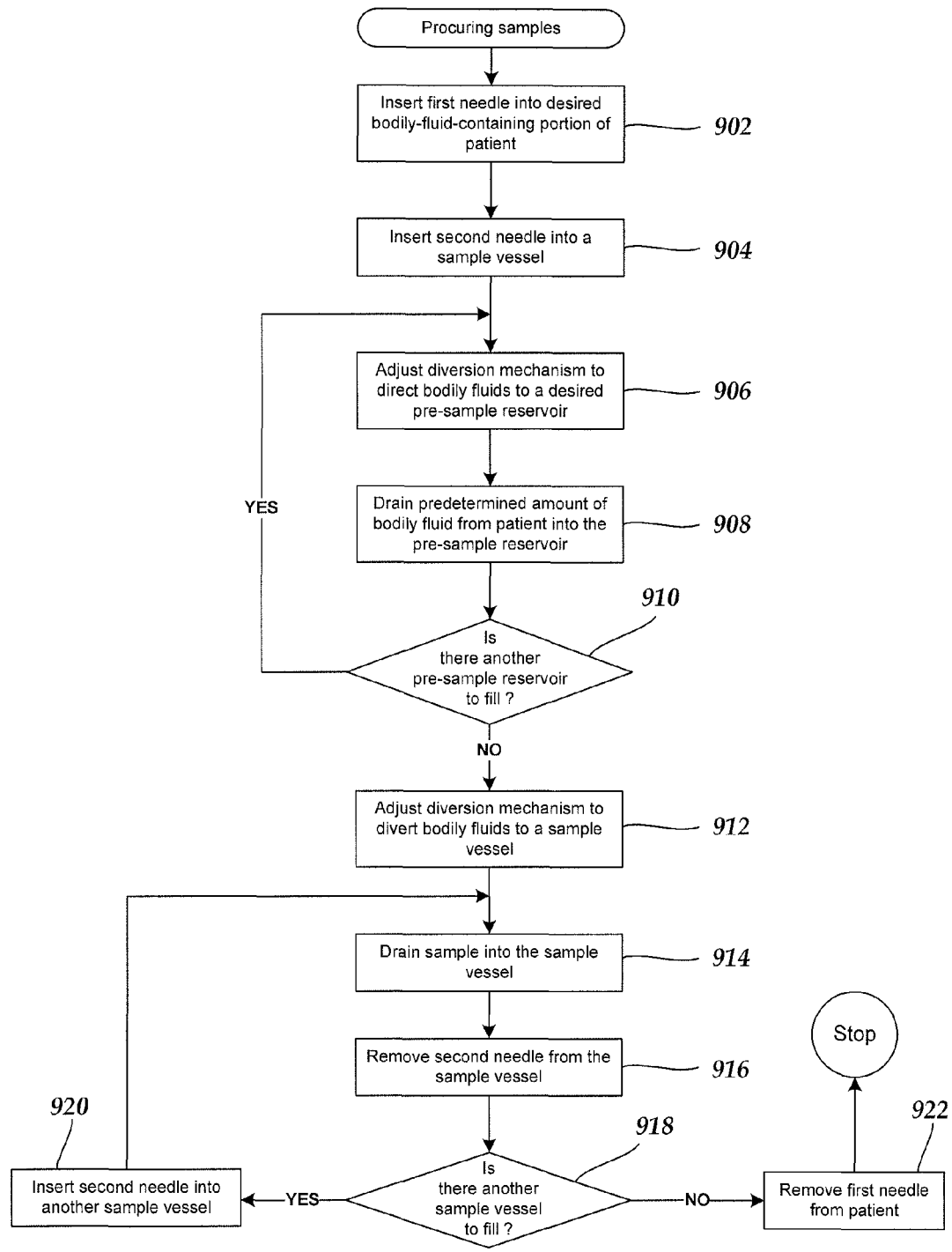
FIG. 9 illustrates a flow diagram showing a second embodiment of exemplary steps used for procuring samples, according to the invention.

FIG. 9 illustrates a flow diagram showing a second embodiment of exemplary steps used for procuring samples. In step 902, a first needle is inserted into a desired bodily-fluid containing portion of a patient. In step 904, a second needle is inserted into a pre-sample reservoir. In step 906, a diversion mechanism is adjusted to direct the flow of bodily fluids to a desired pre-sample reservoir. In step 908, a predetermined amount of bodily fluid is drained from the patient into the pre-sample reservoir. When, in step 910, there is another pre-sample reservoir to drain bodily fluid into, control is passed back up to step 906. Otherwise, control passes to step 912, where the diversion mechanism is adjusted to divert bodily fluids to a sample vessel. In step 914, a predetermined amount of bodily fluid is drained from the patient into the sample vessel. In step 916, the second needle is removed from the sample vessel. When, in step 918, there is another sample vessel to drain bodily fluid into, control is passed to step 920, where the second needle is inserted into another sample vessel, and then control is passed back to step 914. Otherwise, in step 922 the first needle is removed from the patient and the flow ends.

Other alternate embodiments of the methods and systems described above include using a sterile syringe with at least two reservoirs. For example, in at least some embodiments, a sterile syringe with a lumen-containing needle and a removable first reservoir can be used for drawing and collecting pre-sample bodily-fluids from a patient. In at least some embodiments, the volume of collected pre-sample bodily-fluids is equal to, or greater than, the volume of the lumen of the needle. Once the desired amount of pre-sample bodily-fluids are collected, the first reservoir can be removed and a second reservoir can then be attached to the needle, already in place in the vein. In at least some embodiments, sample bodily-fluids can be drawn and collected in the second reservoir and subsequently be transferred to one or more sample vessels to undergo microbial testing.

A study has been performed in which blood was drawn from patients either with or without separating initially-drawn blood into one or more pre-sample reservoirs. The data from the study has been provided below in Table 1.

TABLE 1

|  | No. of false positives | No. of correct negatives |  |
|---|---|---|---|
| Using pre-sample reservoir | 77 | 1911 | 1988 |
| Without using pre-sample reservoir | 48 | 580 | 628 |
|  | 125 | 2491 | 2616 |

In the data shown in Table 1, blood was drawn for microbial testing from patients at a single hospital by a group of licensed phlebotomists. Of the patients from which blood was drawn, 125 patients tested positive for the presence of dermal contaminating microbes (false positives). Of the 2616 patients tested for the presence of microbes, 1988 had an initial volume of drawn blood sequestered into a pre-sample reservoir that was not used for the microbial testing, while 628 patients did not. Of the patients from which a pre-sample reservoir was used, 77 of the 1988 test results were later determined to be false positive results, while 48 of the 628 test results from the patients for which initial blood volumes were used for microbial testing were later determined to be false positive results. The data suggests that fewer false positive test results occur when initial volumes of drawn blood are not used for microbial testing.

A Pearson's Chi-Square Test was performed on the data from Table 1 and is provided below as Formula (1)

$$\frac{[(77 \times 580) - (48 \times 1911)]^2 \times (77 + 48 + 1911 + 580)}{(77 + 1911) \times (48 + 580) \times (1911 + 580) \times (77 + 48)} = 14.91 \quad \text{Formula (1)}$$

For the data shown in Table 1, there are two possible results: a correct (true) negative, and a false positive. The number of degrees of freedom is equal to the number of possible results minus one. A listing of various Chi-square probability values for 1 degree of freedom are provided in Table 2

TABLE 2

|  | Probability | | | | | | | |
|---|---|---|---|---|---|---|---|---|
|  | 0.50 | 0.20 | 0.15 | 0.10 | 0.05 | 0.02 | 0.01 | 0.001 |
| 1 degree of freedom | 0.46 | 1.64 | 2.07 | 2.71 | 3.84 | 5.41 | 6.63 | 10.83 |

As shown in Formula 1, the Chi-square value of the data shown in Table 1 is 14.91, which is higher than the probability of the result occurring by chance alone is less than one time out of a thousand. Thus, the data suggests that fewer false positive test results for the presence of microbes in blood are obtained over conventional methods when initially-drawn volumes of blood are not used in microbial testing.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A system for parenterally procuring bodily-fluid samples from a patient with minimal contamination, the system comprising:
a bodily-fluid withdrawing device, the bodily-fluid withdrawing device comprising
a first sterile needle configured and arranged for insertion into the patient, the first sterile needle comprising a first lumen configured and arranged for withdrawing patient bodily fluids and passing the withdrawn bodily fluids through the first lumen, and
a second sterile needle fluidically coupleable to the first sterile needle, the second sterile needle comprising a second lumen configured and arranged for passing withdrawn bodily fluids through the second lumen;
a vacuum-sealed pre-sample reservoir fluidically coupleable to the first sterile needle, the vacuum-sealed pre-sample reservoirs configured and arranged for collecting and storing patient bodily fluid withdrawn from the bodily-fluid withdrawing device;
a single diversion mechanism coupled to the first sterile needle, the second sterile needle and the pre-sample reservoir, the diversion mechanism configured to selectively establish fluid communication between the first sterile needle and the pre-sample reservoir and fluidically isolate the second sterile needle in a first configuration, and selectively establish fluid communication between the first sterile needle and the second sterile needle and fluidically isolate the pre-sample reservoir in a second configuration; and
at least one vacuum-sealed sample vessel, each of the at least one vacuum-sealed sample vessels configured and arranged for collecting and storing patient bodily fluid withdrawn from the bodily-fluid withdrawing device, each of the at least one sample vessels containing a culture medium;
wherein the second sterile needle is configured and arranged for insertion into the at least one vacuum-sealed sample vessel.

2. The system of claim 1, wherein each of the at least one vacuum-sealed pre-sample reservoirs defines a first mouth with a first septum covering the first mouth, the first septum providing an airtight seal to facilitate the maintenance of a vacuum in the at least one vacuum-sealed pre-sample reservoir.

3. The system of claim 2, wherein the second sterile needle comprises a distal end, the distal end configured and arranged to pass through the first septum and deposit withdrawn patient bodily fluids into each of the at least one vacuum-sealed pre-sample reservoirs.

4. The system of claim 1, wherein each of the at least one vacuum-sealed sample vessels defines a second mouth with a second septum covering the second mouth, the second septum providing an airtight seal to facilitate the maintenance of a vacuum in the at least one vacuum-sealed sample vessel.

5. The system of claim 4, wherein the second sterile needle comprises a distal end, the distal end configured and arranged to pass through the second septum and deposit withdrawn patient bodily fluids into each of the at least one vacuum-sealed sample vessels.

6. The system of claim 1, wherein the bodily-fluid withdrawing device further includes a flexible, sterile tubing with an input end and an output end, the input end coupled to the first lumen of the first sterile needle and the output end coupled to the second lumen of the second sterile needle.

7. The system of claim 1, wherein a first output tube directly couples the diversion mechanism to the at least one pre-sample reservoir such that the diversion mechanism is in fluid communication with the pre-sample reservoir.

8. The system of claim 1, wherein the diversion mechanism comprises a pivotable valve, the pivotable valve configured and arranged to pivot between a first position and a second position, the first position placing the pivotable valve so that withdrawn bodily fluids pass from the first sterile needle to the pre-sample reservoir, the second position placing the pivotable valve so that withdrawn bodily fluids pass from the first sterile needle to the second sterile needle.

9. The system of claim 1, wherein the diversion mechanism comprises an input flow-control block and an output flow-control block slidably-mounted to the input flow-control block, the input flow-control block comprising an input lumen with an input end and an output end, the input end fluidically coupled to the first sterile needle, the output end extending to the output flow-control block.

10. The system of claim 9, wherein the output flow-control block comprises a first output lumen and a second output lumen, the first output lumen and the second output lumen each having an input end and an output end, the input end of both the first output lumen and the second output lumen extending from the input flow-control block, the output end of the first output lumen in fluid communication with the pre-sample reservoir, the output end of the second output lumen in fluid communication with the at least one sample vessel.

11. The system of claim 10, wherein the input flow-control block and the output flow-control block are configured and arranged to slide between a first position and a second position, the first position aligning the input lumen of the input flow-control block with the first output lumen of the output flow-control block, the second position aligning the input lumen of the input flow-control block with the second output lumen of the output flow-control block.

12. A method for parenterally procuring bodily-fluid samples from a patient with reduced contamination, the method comprising:
 providing the system of claim 1;
 inserting the first sterile needle of the system into a selected bodily-fluid-containing portion of the patient;
 draining a predetermined amount of bodily fluids into the vacuum-sealed pre-sample reservoir;
 inserting the second sterile needle into a first vacuum-sealed sample vessel of the at least one vacuum-sealed sample vessels of the system, the first vacuum-sealed sample vessel comprising a first culture medium; and
 draining a predetermined amount of bodily fluids into the first vacuum-sealed sample vessel for incubation in the first culture medium.

13. The method of claim 12, further including removing the second sterile needle from the first vacuum-sealed sample vessel and subsequently inserting the second sterile needle into a second vacuum-sealed sample vessel of the at least one vacuum-sealed sample vessels of the system, the second vacuum-sealed sample vessel comprising a second culture medium.

14. A method for parenterally procuring bodily-fluid samples from a patient with reduced contamination, the method comprising:
 providing the system of claim 1;
 inserting the first sterile needle of the system into a selected bodily-fluid-containing portion of the patient;
 inserting the second sterile needle into a first vacuum-sealed sample vessel of the at least one vacuum-sealed sample vessels of the system;
 adjusting the diversion mechanism of the system to divert withdrawn patient bodily fluids to the pre-sample reservoir of the system; and
 adjusting the diversion mechanism to divert withdrawn patient bodily fluids to the first vacuum-sealed sample vessel.

15. The method of claim 14, further including removing the second sterile needle from the first vacuum-sealed sample vessel and subsequently inserting the second sterile needle into a second vacuum-sealed sample vessel of the at least one vacuum-sealed sample vessels of the system.

16. The method of claim 14, wherein the diversion mechanism comprises a pivotable valve that pivots to divert withdrawn bodily fluids to one of
 the pre-sample reservoir; and
 the first vacuum-sealed sample vessel.

17. The method of claim 14, wherein the diversion mechanism comprises an input flow-control block and an output flow-control block slidably-mounted to the input flow-control block, the output flow-control block slidable along the input flow-control block to divert withdrawn bodily fluids to one of
 the pre-sample reservoir; and
 the first vacuum-sealed sample vessel.

* * * * *